United States Patent [19]

Breuer et al.

[11] 4,003,893
[45] Jan. 18, 1977

[54] 3-HETEROTHIO[(THIOALKYL)THI-OACETYL]CEPHALOSPORANIC DERIVATIVES

[75] Inventors: Hermann Breuer; Uwe D. Treuner, both of Regensburg, Germany

[73] Assignee: E. R. Squibb & Sons, Inc., Princeton, N.J.

[22] Filed: Oct. 11, 1974

[21] Appl. No.: 513,978

[52] U.S. Cl. .......................... 260/243 C; 424/246; 260/332.2 A; 260/347.2; 260/470; 260/481 R; 260/515 M; 260/526 S; 260/544 S; 260/544 Y

[51] Int. Cl.² ...................................... C07D 501/50
[58] Field of Search ............................ 260/243 CS

[56] References Cited
FOREIGN PATENTS OR APPLICATIONS 948,076  1/1964  United Kingdom ........... 260/243 C

OTHER PUBLICATIONS

Lewis et al., Antimicrobial Agents & Chemeotherapy 1968 pp. 109-114 (1969).

*Primary Examiner*—Nicholas S. Rizzo
*Assistant Examiner*—Diana G. Rivers
*Attorney, Agent, or Firm*—Lawrence S. Levinson; Merle J. Smith

[57] ABSTRACT

3-Heterothio[(thioalkyl)thioacetyl]cephalosporin derivatives which have the formula

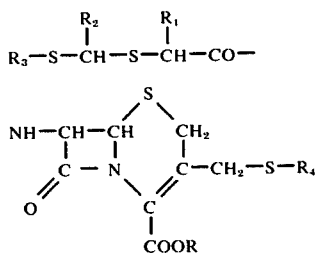

wherein R is hydrogen, lower alkyl, phenyl-lower alkyl, tri(lower alkyl)silyl, a salt forming ion, or the group

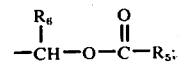

$R_1$ is hydrogen, lower alkyl, phenyl, thienyl of furyl; $R_2$ and $R_6$ each is hydrogen or lower alkyl; $R_3$ and $R_5$ each is lower alkyl, phenyl or phenyl-lower alkyl; and $R_4$ is a five- or six-membered nitrogen and/or sulfur or oxygen-containing ring system; are useful as antibacterial agents.

13 Claims, No Drawings

3-HETEROTHIO[(THIOALKYL)THIOACETYL]-CEPHALOSPORANIC DERIVATIVES

SUMMARY OF THE INVENTION

This invention relates to new [(thioalkyl)thioacetyl]-cephalosporin derivatives of the formula

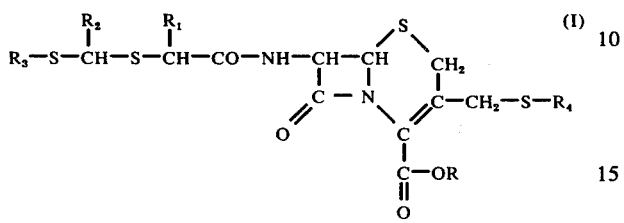

R represents hydrogen, lower alkyl, phenyl-lower alkyl, tri(lower alkyl)silyl, a salt forming ion or the group

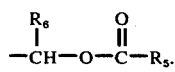

$R_1$ represents hydrogen, lower alkyl, phenyl, thienyl or furyl.

$R_2$ and $R_6$ each represents hydrogen or lower alkyl.

$R_3$ and $R_5$ each represents lower alkyl, phenyl or phenyl-lower alkyl.

$R_4$ is a five-membered or six-membered nitrogen or nitrogen and sulfur or oxygen-containing heterocyclic group including oxadiazole, thiatriazole, thiadiazole, tetrazole, 1-oxopyridine and their lower alkyl substituted analogs, particularly the heterocyclics having the structures

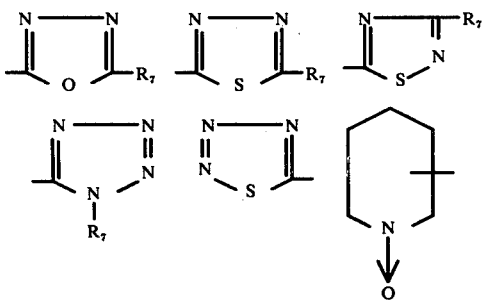

wherein $R_7$ represents hydrogen or lower alkyl.

DETAILED DESCRIPTION OF THE INVENTION

The various groups represented by the symbols have the meanings defined below and these definitions are retained throughout this specification.

The lower alkyl groups are straight or branched chain hydrocarbon groups containing 1 to 8 carbon atoms, preferably 1 to 4 carbons. Examples of the type of these groups are methyl, ethyl, propyl, isopropyl, butyl, t-butyl, pentyl, isopentyl, etc. The phenyl-lower alkyl groups include such lower alkyl groups attached to a phenyl (or two phenyl groups), e.g., benzyl, phenethyl, benzhydryl, etc.

The salt forming ions represented by R are metal ions, e.g., alkali metal ions such as sodium or potassium, alkaline earth metal ions such as calcium or magnesium, or an amine salt ion, of which a number are known for this purpose, for example, lower alkylamines like methylamine or triethylamine, aralkylamines like dibenzylamine, N,N-dibenzylethylenediamine, N-ethylpiperidine, etc.

Preferred embodiments of this invention are as follows:

R is hydrogen, alkali metal, trimethylsilyl or

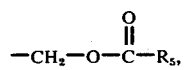

especially hydrogen, pivaloyloxymethyl, sodium or potassium, $R_5$ is lower alkyl.

$R_1$ is hydrogen, lower alkyl of 1 to 4 carbons, phenyl, furyl or thienyl, especially hydrogen and phenyl.

$R_2$ and $R_6$ each is hydrogen or lower alkyl of 1 to 4 carbons, especially hydrogen.

$R_3$ is lower alkyl, especially methyl, or phenyl.

$R_4$ is thiadiazole, tetrazole and their methyl substituted analogs, especially, 1,3,4-thiadiazole, 5-methyl-1,3,4-thiadiazole, tetrazole and 1-methyltetrazole.

The new derivatives of [(thioalkyl)thioacetyl]-cephalosporins of this invention are produced by reacting 7-aminocephalosporanic acid (7-ACA) (or derivatives wherein $R_3$ is other than hydrogen) with a mercaptan $HS-R_4$ at a pH of about 8 – 8.5 to obtain the derivative of the formula

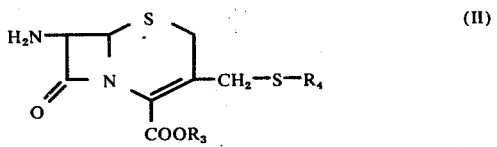

The product of formula II is then acylated on the amino group with a [(thioalkyl)thio]acetic acid of the formula

or an activated derivative of the former (II).

The activated derivatives referred to include, for example, the acid chloride or reaction product with an anhydride forming reagent such as ethylchloroformate, benzoyl chloride, pivaloyl chloride, etc., or with bisimidazolecarbonyl, dicyclohexylcarbodiimide, p-nitrophenol or the like.

According to a preferred modification, the 7-aminocephalosporanic acid derivative of formula II preferably an ester like the benzhydryl ester, and the acid of formula III are dissolved in an organic solvent like tetrahydrofuran and dicyclohexylcarbodiimide, in an organic solvent like the one mentioned above, is added at a reduced temperature of about 0° C. The dicyclohexylurea formed during the reaction is removed and the product is recovered from the filtrate. The benzhydryl group is removed, for example, by treatment with trifluoroacetic acid and anisole.

According to another modification, reaction between the 7-aminocephalosporanic acid compound of formula II and the [(thioalkyl)thio]acetic acid is effected, for example, by converting the latter to the acid chloride with an agent such as thionyl chloride and adding the acid chloride in an organic solvent like acetone, at a low temperature, e.g., 0° C. or below, to a mixture of the 7-aminocephalosporanic acid derivative of formula II, and a salt forming organic base, such as triethylamine, pyridine or the like, in an inert organic solvent such as chloroform, methylene chloride, dioxane, benzene or the like. The product of the reaction is then isolated by conventional procedures, e.g., by concentration, solvent extraction or evaporation of the solvent.

Alternatively, 7-ACA or a derivative thereof ($R_3$ in formula II is other than hydrogen), can be first acylated as described in our copending application Ser. No. 495,598, filed Aug. 8, 1974, then the product of this reaction is made to react with the mercaptan HS-$R_4$ at an alkaline pH, e.g., about 7.8.

Any of the salts can be produced from the free acid by conventional treatment, e.g., potassium ethyl hexanoate, sodium bicarbonate or the like.

When R is the acyloxymethyl group

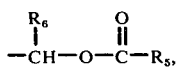

this group can be introduced into the 7-aminocephalosporanic acid moiety prior to the reaction with the [(thioalkyl)-thio]acetic acid or derivative by treatment with one to two moles of a halomethyl ester of the formula

 (IV)

wherein hal is halogen, preferably chlorine or bromine, in an inert organic solvent such as dimethylformamide, acetone, dioxane, benzene or the like, at about ambient temperature or below.

The [(thioalkyl)thio]acetic acid of formula III is produced by reacting a mercaptoacetic acid of the formula

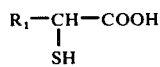 (V)

with a halogenated compound of the formula

 (VI)

in the presence of a base like triethylamine in a solvent like tetrahydrofuran and hydrolyzing the ester formed in the process.

Alternatively, when the acid halide is used to react with the 7-aminocephalosporanic acid compound, a mercaptan $R_3$-SMe (wherein Me is a metal like potassium) is made to react with a haloester of the formula

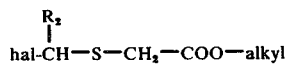 (VII)

to obtain the intermediate of the formula

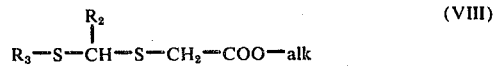 (VIII)

Treatment with a base, e.g., an alkali metal hydroxide, converts the ester to a salt which is then converted to the acid chloride with a halogenating agent like oxalyl chloride.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They can be used as antibacterial agents to combat infections due to organisms such as those named above, and in general may be utiized in a manner similar to cephradine and other cephalosporins. For example, a compound of formula I or a physiologically acceptable salt thereof can be used in various animal species in an amount of about 1 to 150 mg./kg., daily, orally or parenterally, in single or two to four divided doses to treat infections of bacterial origin, for example, 5.0 mg./kg. is effective in mice.

Up to about 600 mg. of a compound of formula I or a physiologically acceptable salt thereof is incorporated in an oral dosage form such as tablet, capsule or elixir or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

[(Methylthio)methyl]thioacetic acid, triethylamine salt 30.4 ml. (0.22 mol.) of triethylamine are added to 9.21 gms. (0.1 mol.) of mercaptoacetic acid in 100 ml. of absolute tetrahydrofuran. 9.65gms. of (methylthio)-methyl chloride dissolved in 10 ml. of tetrahydrofuran are added dropwise at 0°. The mixture is stirred at room temperature for two days. The mixture is filtered and the filtrate is concentrated under vacuum. The residue [(methylthio)-methyl]thioacetic acid, triethylamine salt is used further without purification.

EXAMPLE 2

[(Methylthio)methyl]thioacetyl chloride

The product of Example 1 is dissolved in 125 ml. of methylene chloride and a solution of 25.4 gms. of oxalyl chloride in 50 ml. of methylene chloride is added dropwise at 110°. This is stirred for one hour at room temperature and then concentrated. Ether is added to the residue and the mixture is filtered. The filtrate is concentrated and the residue is distilled under vacuum to obtain 6.6 gms. of [(methylthio)methyl]thio]acetyl chloride, b.p. $_{0.01}$ 71°–74°.

EXAMPLE 3

3-[(Acetyloxy)methyl]-7-[[[[(methylthio)methyl]-thio]acetyl]-amino]-8-oxo-5-thia-1-azabicyclo[4.2.-0]oct-2-ene-2-carboxylic acid 5.44 gms. of 7-aminocephalosporanic acid are brought into solution in a mixture of 35 ml. of water and 35 ml. of acetone at 0°–5° by the addition of saturated sodium bicarbonate solution. A solution of 4.42 gms. of [(methylthio)methyl]thio]acetyl chloride in 10 ml. of acetone are added dropwise at a pH of about 7.5. The pH is held at 7.5 by the addition of sodium bicarbonate. After 30 minutes, 100 ml. of ethyl acetate are added and the pH is brought to 1.5 with 2N hydrochloric acid. The ethyl acetate solution is concentrated, extracted with methylene chloride, filtered, concentrated and the product, 3-[(acetyloxy)methyl]-7-[[[[(methylthio)methyl]thio]acetyl]-amino]-8-oxo-5-thia-1-azabicyclo[4.2.0]oct-2-ene-2-carboxylic acid, is precipitated from the residue with ethyl acetate/petroleum ether, m.p. 118°–120° (dec.).

EXAMPLE 4

3-[(Acetyloxy)methyl]-7-[[[[(methylthio)methyl]-thio]acetyl]-amino]-8-oxo-5-thia-1-azabicyclo[4.2.-0]oct-2-ene-2-carboxylic acid, potassium salt 1.5gms. of 3-[(acetyloxy)methyl]-7-[[[[(methyl-thio)methyl]thio]acetyl]amino]-8-oxo-5-thia-1-azabicyclo-[4.2.0]oct-2-ene-2-carboxylic acid dissolved in 5 ml. of methanol are added to a 2N solution of potassium ethyl hexanoate in n-butanol to obtain 1.3 gms. of crystalline 3[(acetyloxy)methyl]-7-[[[[(methylthio)-methyl]thio]acetyl]-amino]-8-oxo-5-thia-1-azabicyclo[4.2.0]oct-2-ene-2-carboxylic acid salt, m.p. 120°–122° (dec.).

EXAMPLE 5

DL-α-[[(Methylthio)methyl]thio]benzeneacetic acid, (methylthio)methyl ester 16.8 gms. of α-phenylmercaptoacetic acid and 28.9 gms. of (methylthio)methyl chloride are dissolved in 100 ml. of absolute tetrahydrofuran and 41.4 ml. of triethylamine are added dropwise at 0°. The mixture is stirred overnight at room temperature, filtered, concentrated and the residue is distilled under vacuum to obtain 12.9 gms. of DL-α-[[(methylthio)methyl]thio]-benzeneacetic acid, (methylthio) methyl ester, b.p.$_{0.05}$ 178°–180°.

EXAMPLE 6

DL-α-[[(Methylthio)methyl]thiobenzeneacetic acid 2.9 gms. of DL-α-[[(methylthio)methyl]thio]benzene acetic acid, (methylthio)methyl ester are dissolved in 10 ml. of ethanol. 20 ml. of 1N alcoholic sodium hydroxide solution are added and the mixture is permitted to stand overnight. This is then concentrated, the residue is dissolved in water, the aqueous solution is extracted once with ether, then acidified and the oil is extracted with ether. After drying with magnesium sulfate and evaporating the solvent 1.8 gms. of DL-α-[[(methylthio)methyl]thio]benzeneacetic acid are obtained as an oil.

EXAMPLE 7

DL-3-[(acetyloxy)methyl]-7β-[[[[(methylthio)methyl]thio]-phenylacetyl]amino]-8-oxo-5-thia-1-azabicyclo[4.2.0]oct-2-ene-2-carboxylic acid, diphenylmethyl ester A solution of 4.54 gms. (0.022 mol.) of dicyclohexylcarbodiimide in 40 ml. of absolute tetrahydrofuran is added at 0° to a solution of 8.76 gms. (0.02 mol.) of 7-aminocephalosporanic acid, diphenylmethyl ester and 5.47 gms. (0.024 mol.) of DL-α-[[(methylthio)methyl]thio]-benzeneacetic acid in 100 ml. of absolute tetrahydrofuran. This is stirred for 90 minutes at 0° and 90 minutes at room temperature, then filtered and the filtrate is concentrated. The residue (9.8 gms.) is purified on a column of 500 gms of Kieselgel (Merck). The column is eluted with toluene/dioxane (80:20) and fractions of about 40 ml. each are collected. The product, DL-3-[(acetyloxy)methyl]-7β-[[[[(methylthio)-methyl]thio]phenylacetyl]amino]-8-oxo-5-thia-1-azabicyclo[4.2.0]oct-2-ene-2-carboxylic acid, diphenylmethyl ester, is obtained from fractions 13, 14 and 15 in chromatographically pure form.

EXAMPLE 8

DL-3-[(Acetyloxy)methyl]-7β-[[[[(methylthio)methyl]thio]phenylacetyl]amino]-8-oxo-5-thia-1-azabicyclo[4.2.0]oct-2-ene-2-carboxylic acid 1.9 gms. of the product of Example 7 are dissolved in 14 ml. of anisole and 39 ml. of trifluoroacetic acid are added while cooling with ice. This is then concentrated after 10 minutes. The residue is purified by dissolving in 10 ml. of methanol and treating with a 10% solution of dicyclohexylamine in isopropanol. 1.4 gms. of the dicyclohexylamine salt of D-3-[(acetyloxy)methyl]-7β-[[[[(methylthio)methyl]thio]phenylacetyl]amino]-8-oxo-5-thia-1-azabicyclo[4.2.0]oct-2-ene-2-carboxylic acid crystallizes, m.p. 174°–175° (dec.). The salt is suspended in a little water while cooling with ice, layered over with ethyl acetate and acidified. From the ethyl acetate extract are isolated 1.2 gms. of pure DL-3-[(acetyloxy)methyl]-7β-[[[[(methylthio)-methyl]-thio]phenylacetyl]amino]-8-oxo-5-thia-1-azabicyclo-[4.2.0]oct-2-ene-2-carboxylic acid.

EXAMPLE 9

DL-3-[(Acetyloxy)methyl]-7β-[[[[(methylthio)methyl]thio]-phenylacetyl]-8-oxo-5-thia-1-axabicyclo[4.2.0]oct-2-ene-2-carboxylic acid, sodium salt The product of Example 8 is neutralized with an equimolar amount of aqueous sodium bicarbonate solution. The solution is filtered and freeze dried to obtain DL-3-[(acetyloxy)methyl]-7β-[[[[(methylthio)-methyl]thio]phenylacetyl]amino]-8-oxo-5-thia-1-azabicyclo[4.2.0]oct-2-ene-2-carboxylic acid, sodium salt, m.p. 185°–186° (dec.).

EXAMPLE 10

[[(Phenylthio)methyl]thio]acetic acid, methyl ester 14.8 gms. of potassium thiophenolate are combined with 15.4 gms. of (chloromethyl)thioacetic acid, methyl ester in 100 ml. of dimethylformamide while warming. This is stirred overnight at room temperature and then concentrated in a rotary evaporator. Water and ether are added to the residue. The ether phase is dried with magnesium sulfate, concentrated and distilled to obtain 16 gms. of [[(phenylthio)methyl]thio]acetic acid, methyl ester, b.p.$_{0.01}$ 123°–130°.

EXAMPLE 11

[[(Phenylthio)methyl]thio]acetic acid, potassium salt 50 ml. of 2N potassium hydroxide in isopropanol are added to a solution of 20.8 gms. of [[(phenylthio)methyl]-thio]acetic acid, methyl ester in 150 ml. of isopropanol. 20 gms. of [[(phenylthio)methyl]thio]acetic acid, potassium salt crystallize, m.p. 280°–283° (dec.).

EXAMPLE 12

[[(Phenylthio)methyl]thio]acetyl chloride 5.1 gms. of [[(phenylthio)methyl]thio]acetic acid, potassium salt are treated with 5 gms. of oxalyl chloride in 10 ml. of methylene chloride at 0°–5° to obtain 3.4 gms. of [[(phenylthio)methyl]thio]acetyl chloride which is used further without purification.

EXAMPLE 13

DL-3-[(Acetyloxy)methyl]-7-[[[[(phenylthio)methyl]thio]-acetyl]amino]-8-oxo-5-thia-1-azabicyclo[4.2.0]oct-2-ene-2-carboxylic acid 3.1 gms. of 7-aminocephalosporanic acid and 3.4 gms. of [[(phenylthio)methyl]thio]acetyl chloride are treated according to the procedure of Example 3 to obtain DL-3-[(acetyloxy)methyl]-7-[[[[(phenylthio)-methyl]thio]acetyl]-amino]-8-oxo-5-thia-1-azabicyclo[4.2.0]oct-2-ene-2-carboxylic acid. For purification, this product is converted to its potassium salt with potassium ethyl hexanoate. The reaction mixture is acidified and extracted with ethyl acetate to obtain the purified free acid. This is dissolved in methylene chloride and petroleum ether is added to the solution. The product precipitates in amorphous solid form.

EXAMPLE 14

[[[(Phenylmethyl)thio]methyl]thio]acetic acid, methyl ester

A mixture of 12.4 gms. of benzyl mercaptan, 15.4 gms. of (chloromethyl)thioacetic acid, methyl ester and 14.0 ml. of triethylamine in 100 ml. of tetrahydrofuran are permitted to stand overnight. The mixture is filtered, concentrated and distilled to obtain [[[(phenylmethyl)thio]methyl]thio]acetic acid, methyl ester, b.p.$_{0.01-0.05}$ 150°–160°.

EXAMPLE 15

[[[(Phenylmethyl)thio]methyl]thio]acetic acid, potassium salt 26.0 ml. of 2N methanolic potassium hydroxide are added to 10 gms. of the product of Example 14 in 50 ml. of isopropanol to obtain 7.8 gms. of [[[(phenylmethyl)thio]-methyl]thio] acetic acid, potassium salt, m.p.> 230°.

EXAMPLE 16

[[[(Phenylmethyl)thio]methyl]thio]acetyl chloride 6.9 gms. of the product of Example 15 in 25 ml. of methylene chloride are treated at room temperature with 6.5 gms. of oxalyl chloride in 9 ml. of methylene chloride according to the procedure of Example 2. 5.9 gms. of the product, [[[(phenylmethyl)thio]methyl]-thio]acetyl chloride, are obtained as an oil which is used further without purification.

EXAMPLE 17

DL-3-[(Acetyloxy)methyl]-7β-[[[[(phenylmethyl)-thio]methyl]-thio]acetylamino]-8-oxo-5-thia-1-azabicyclo[4.2.0]oct-2-ene-2-carboxylic acid 2.7 gms. of 7-aminocephalosporanic acid with an equimolar amount of triethylamine are dissolved in a mixture of 30 ml. of water and 30 ml. of acetone. A solution of 2.9 gms. of [[[(phenylmethyl)thiomethyl]-thio]acetyl chloride is added dropwise at 0° to 5° with stirring and the pH is held at 7–7.5 by the simultaneous addition of triethylamine. The mixture is stirred for two hours at 0°–5° and then worked up by the procedure of Example 3. The yield of product, DL-3-[(acetoxy)methyl]-7β-[[[[(phenylmethyl)thio]methyl]-thio]acetylamino]-8-oxo-5-thia-1-azabicyclo[4.2.0]oct-2-ene-2-carboxylic acid, is 2.4 gms. This product is purified by dissolving in 10 ml. of methanol and neutralizing by means of a 10% solution of dicyclohexylamine in isopropanol. 2.3 gms. of the dicyclohexylamine salt crystallize, m.p. 168°–170° (dec.). To obtain the free acid, the salt is suspended in 100 ml. of ethyl acetate, 100 ml. of water are added and this is acidified with 1N hydrochloric acid. On concentrating the ethyl acetate phase, an oily residue is obtained which solidifies upon trituration with petroleum ether. The product, DL-3-[(acetyloxy)methyl]-7β-[[[[(phenylmethyl)-thio]methyl]thio]acetylamino]-8-oxo-5-thia-1-azabicyclo-[4.2.0]oct-2-ene-2-carboxylic acid, melts at 75°–78° (dec.).

EXAMPLE 18

DL-3-[(Acetyloxy)methyl]-7β[[[[(phenylmethyl)-thio]methyl]thio]-acetylamino]-8-oxo-5-thia-1-azabicyclo[4.2.0]oct-2-ene-2-carboxylic acid, sodium salt 1.1 gm. of the acid obtained in Example 17 are dissolved in 20 ml. of methanol and the solution is neutralized with 22 ml. of 0.1N sodium bicarbonate solution. This is filtered and the methanol is evaporated in a rotary evaporator. The residual aqueous solution is freeze dried to obtain 1.1 gm. of DL-3-[(acetyloxy)methyl]-7β-[[[[(phenylmethyl)thio]methyl]-thio]acetylamino]-8-oxo-5-thia-1-azabicyclo[4.2.0]oct-2-ene-2-carboxylic acid, sodium salt, m.p. 110°–112° (dec.).

EXAMPLE 19

3-[[(5-Methyl-1,3,4-thiadiazol-2-yl)thio]methyl]-7-amino-8-oxo-5-thia-1-azabicyclo[4.2.0]oct-2-ene-2-carboxylic acid A mixture of 13.6 g. (0.5 M) of 7-aminocephalosporanic acid (7-ACA) in 100 ml. of water and 50 ml. of acetone are brought to pH 8 with sodium hydroxide while stirring. 9.8 g. (0.57 M) of 2-methyl-1,3,4-thiadiazole-5-thiol are added and the mixture is heated at 80° for four hours. After cooling to 5°, this is acidified to pH 3.5 with dilute hydrochloric acid and stirred for 15 minutes. The precipitated solid is filtered under suction and washed with acetone. This 3-[[(5-methyl-1,3,4-thiadiazol-2-yl)thio]-methyl]-7-amino-8-oxo-5-thia-1-azabicyclo[4.2.0]oct-2-ene-2-carboxylic acid is purified by dissolving in sodium bicarbonate solution and reprecipitating with 2N hydrochloric acid; yield 12.7 g., m.p. 206°.

EXAMPLE 20

3-[[(3-Methyl-1,2,4-thiadiazol-5-yl)thio]methyl]-7-amino-8-oxo-5-thia-1-azabicyclo[4.2.0]oct-2-ene-2-carboxylic acid By substituting 3-methyl-1,2,4-thiadiazole-5-thiol for the 2-methyl-1,3,4-thiadiazole-5-thiol in the procedure of Example 19, 11.6 g. of 3-[[(3-methyl-1,2,4-thiadiazol-5-yl)thio]methyl]-7-amino-8-oxo-5-thia-1-azabicyclo[4.2.0]oct-2-ene-2-carboxylic acid, m.p. 186° (dec.) are obtained.

EXAMPLE 21

3-[[(1-Methyl-1H-tetrazol-5-yl)thio]methyl]-7-amino-8-oxo-5-thia-1-azabicyclo[4.2.0]oct-2-ene-2-ene-2-carboxylic acid By substituting 0.57 M of 1-methyl-1H-tetrazol-5-thiol for the 2-methyl-1,3,4-thiadiazol-5-thiol in the procedure of Example 19,3-[[(1-methyl-1H-tetrazol-5-yl)thio]-methyl]-7-amino-8-oxo-5-thia-1-azabicyclo[4.2.0]oct-2-ene-2-carboxylic acid is obtained.

EXAMPLE 22

3-[[(5-Methyl-1,3,4-thiadiazol-2-yl)thio]methyl]-7-amino-8-oxo-5-thia-1-azabicyclo[4.2.0]oct-2-ene-2-carboxylic acid, diphenylmethyl ester 18 g. of 7-amino-3-[[(5-methyl-1,3,4-thiadiazol-5-yl)thio]methyl]-8-oxo-5-thia-1-azabicyclo[4.2.0]oct-2-ene-2-carboxylic acid are suspended in 350 ml. of tetrahydrofuran. 4.1 ml. of 70% perchloric acid are added dropwise. After 30 minutes, a slightly turbid solution forms. This solution is filtered and to the filtrate is added dropwise with stirring 12 g. of diphenyldiazomethane and 20 ml. of tetrahydrofuran. After three hours, the reaction mixture is poured into 2 liters of absolute ether. The solid, light brown precipitate, which is the perchloric acid salt of the desired product, is dried over Kieselgel in a desiccator. To obtain the base, the perchloric acid salt is dissolved in water and treated with the calculated equivalent of potassium bicarbonate. The aqueous solution obtained is extracted with chloroform. The chloroform phase is treated with activated carbon and sodium sulfate to obtain the 10 g. of the product, 7-amino-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester, as a light brown powder, m.p. 157°–159°. The product is recrystallized from tetrahydrofuran/petroleum ether. The isomeric thiadiazolyl derivative is similarly obtained from the product of Example 20.

EXAMPLE 23

3-[[(1-Methyl-1H-tetrazol-5-yl) thio]methyl]-7-amino-8-oxo-5-thia-1-azabicyclo[4.2.0]oct-2-ene-2-carboxylic acid, diphenylmethyl ester The product, 7-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester, m.p. 168°–169° (dec.), is obtained by the procedure of Example 22 utilizing as starting material 7-amino-3-[[(1-methyl-1H-tetrazol-5-yl)-thio]methyl]-8-oxo-5-thia-1-azabicyclo[4.2.0]oct-2-ene-2-carboxylic acid.

EXAMPLE 24

3-[[(1-Methyl-1H-tetrazol-5-yl)thio]methyl]-7β-[[[[(methylthio)methyl]thio]acetyl]amino]-8-oxo-5-thia-1-azabicyclo[4.2.0]oct-2-ene-2-carboxylic acid 6.56 g. (0.02 Mol.) of 3-[[(1-methyl-1H-tetrazol-5-yl)thio]methyl]-7-amino-8-oxo-5-thia-1-azabicyclo[4.2.0]-oct-2-ene-2-carboxylic acid are suspended in a mixture of 60 ml. of water and 60 ml. of acetone and brought into solution by the dropwise addition of triethylamine. The pH of the clear solution reaches about 9.0. The solution is cooled to 0°–5° and a solution of 5.13 g. (0.03 Mol.) of [(methylthio)methyl]thioacetyl chloride in 60 ml. of anhydrous acetone is added. By the simultaneous addition of triethylamine dissolved in acetone, the pH is maintained at 7 – 7.5. After the addition, the mixture is stirred 30 minutes at 0°–5°, then 400 ml. of ethyl acetate are added to the clear mixture and it is acidified to pH 1.5 with 2N hydrochloric acid. A small amount of unreacted starting material which has precipitated is filtered off. The layers are then separated and the aqueous phase is extracted twice with ethyl acetate. The combined ethyl acetate phases are washed with water, treated with activated carbon, dried with magnesium sulfate and concentrated. The oily residue solidifies upon trituration with ether giving 5.1 g. of crude product.

The crude 3-[[(1-methyl-1H-tetrazol-5-yl)thio]methyl]-7β-[[[[(methylthio)methyl]thio]acetyl]amino]-8-oxo-5-thia-1-azabicyclo[4.2.0]oct-2-ene-2-carboxylic acid is purified by conversion to its dicyclohexylamine salt. The crude material is dissolved in 50 ml. of methanol. The slightly turbid solution is treated with activated carbon and filtered. 2.2 g. of dicyclohexylamine are added to the filtrate. Upon the addition of 50 ml. of isopropanol, the dicyclohexylamine salt of the product crystallizes, yield, 3.5 g., m.p. 178°–180° (dec.). The purified free acid is obtained by suspending the cyclohexylamine salt in 200 ml. of ethyl acetate, adding 200 ml. of water and adjusting the pH to 1.5 by stirring. 1.45 g. of the purified product acid are isolated from the organic phase, m.p. 74°–79° (dec.).

EXAMPLE 25

3-[[(1-Methyl-1H-tetrazol-5-yl)thio]methyl]-7β-[[[[(methylthio)methyl]thio]acetyl]-8-oxo-5-thia-1-azabicyclo[4.2.0]oct-2-ene-2-carboxylic acid, sodium salt 1.30 g. of the free acid of Example 24 are dissolved in 20 ml. of acetone and 28 ml. of a 0.1 N sodium bicarbonate solution are added. The acetone is evaporated off in a rotary evaporator. The residual aqueous solution is filtered and freeze dried, yield 1.25 g. of 3-[[(methyl-1H-tetrazol-5-yl)thio]methyl]-7β-[[[[(methylthio)methyl]thio]acetyl]-8-oxo-5-thia-1-azabicyclo[4.2.0]oct-2-ene-2-carboxylic acid, sodium salt, m.p. 100°–110° (dec.).

EXAMPLE 26

3-[[(1-Methyl-1H-tetrazol-5-yl)thio]methyl]-7β-[[[[(methylthio)methyl]thio]phenylacetyl]amino]-8-oxo-5-thia-1-azabicyclo[4.2.0]oct-2-ene-2-carboxylic acid diphenylmethyl ester 2.84 g. of DL-α-[[(methylthio)methyl]thio]benzeneacetic acid and 4.40 g. of 3-[[(1-methyl-1H-tetrazol-5-yl)thio]methyl]-7-amino-8-oxo-5-thia-1-azabicyclo[4.2.0]oct-2-ene-2-carboxylic acid, diphenylmethyl ester are dissolved in 180 ml. of tetrahydrofuran. This is cooled to 0°–5° and to this solution is added dropwise with stirring a solution of 2.3 g. of dicyclohexylcarbodiimide in 20 ml. of tetrahydrofuran. The reaction mixture is stirred for 90 minutes at 0°–5° and 90 minutes at room temperature. The precipitated dicyclohexylurea is filtered off and the filtrate is concentrated in vacuum. The residue is dissolved in 500 ml. of ethyl acetate and the solution is extracted three times with dilute sodium bicarbonate solution and twice with water, treated with activated carbon, dried with magnesium sulfate and concentrated. A little ethyl acetate is added to the residue and the product, 3-[[(1-Methyl-1H-tetrazol-5-yl)thio]methyl]-7β-[[[[(methylthio)methyl]thio]-phenylacetyl]amino]-8-oxo-5-thia-1-azabicyclo[4.2.-0]oct-2-ene-2-carboxylic acid diphenylmethyl ester crystallizes, yield 3.5 g., m.p. 90°–100° (dec.). Addition of petroleum ether to the mother liquor yields another 3 g. of somewhat impure product.

EXAMPLE 27

3-[[(1-Methyl-1H-tetrazol-5-yl)thio]methyl]-7β-[[[[(methylthio)methyl]thio]phenylacetyl]amino-8-oxo-5-thia-1-azabicyclo[4.2.0]oct-2-ene-2-carboxylic acid 1.5 g. of the diphenylmethyl ester of Example 26 are added to a cooled mixture (0°–5°) of 9 ml. of anisole and 31 ml. of trifluoroacetic acid and allowed to react for 10 minutes. Then the trifluoroacetic acid is evaporated in vacuum and ether is added to the residue. The precipitated product, 3-[[(1-Methyl-1H-tetrazol-5-yl)thio]methyl]-7β-[[[[(methylthio)methyl]thio]-phenylacetyl]amino-8-oxo-5-thia-1-azabicyclo[4.2.-0]oct-2-ene-2-carboxylic acid is filtered under suction, yield 0.8 g., m.p., 97°–100° (dec.).

EXAMPLE 28

3-[[1-Methyl-1H-tetrazol-5-yl)thio]methyl]-7β-[[[[(methylthio)methyl]thio]phenylacetyl]amino]-8-oxo-5-thia-1-azabicyclo[4.2.0]oct-2-ene-2-carboxylic acid, sodium salt 0.7 g. of the product of Example 27 are dissolved in 10 ml. of acetone. 0.1 N sodium bicarbonate solution is added to the sodium until pH 6.5 is reached. The acetone is distilled off in a rotary evaporator, the aqueous solution is filtered and freeze-dried, 0.6 g. of 3-[[1-Methyl-1H-tetrazol-5-yl)thio]methyl]-7β-[[[[(methylthio)methyl]thio]phenylacetyl]amino]-8-oxo-5-thia-1-azabicyclo[4.2.0]oct-2-ene-2-carboxylic acid, sodium salt are obtained, m.p. 130°–135° (dec.).

EXAMPLE 29

3-[[(1-Methyl-1H-tetrazol-5-yl)thio]methyl]-8-oxo-7β-[[[[(phenylmethyl)thio]methyl]thio]acetyl]amino-5-thia-1-azabicyclo[4.2.0]oct-2-ene-2-carboxylic acid 3.28 g. (0.01 M) of 3-[[(1-methyl-1H-tetrazol-5-yl)thio]methyl]-7-amino-8-oxo-5-thia-1-azabicyclo[4.2.0]oct-2-ene-2-carboxylic acid are suspended in a mixture of 30 ml. of acetone and 30 ml. of water and brought into solution by the addition of an equivalent amount of triethylamine. This is cooled to 0°–5° and to this added dropwise with stirring over a period of one hour a solution of 2.9 g. (0.012 Mol.) of [[[(phenylmethyl)thio]methyl]thio]acetyl chloride in 30 ml. of acetone. Simultaneously a solution of triethylamine in acetone is added to maintain the pH at 7–7.5. This is stirred for 30 minutes more, ethyl acetate is added and it is acidified to pH 1.5 with 2 N hydrochloric acid. The organic phase is concentrated and petroleum ether is added to obtain 2.0 gm. of 3-[[(1-Methyl-1H-tetrazol-5-yl)thio]methyl]-8-oxo-7β-[[[[(phenylmethyl)thio]methyl]thio]acetyl]amino-5-thia-1-azabicyclo[4.2.-0]oct-2-ene-2-carboxylic acid, m.p. 70°–72° (dec.).

The crude acid is purified by conversion to the dicyclohexylamine salt by dissolving it in 10 ml. of methanol and bringing the pH to 7.5 with a 10% solution of dicyclohexylamine in ethanol. 1.6 g. of the dicyclohexylamine salt crystallize, m.p. 140°–141° (dec.).

The dicyclohexylamine salt is suspended in 100 ml. of ethyl acetate, 100 ml. of water are added and this is acidified with 2 N hydrochloric acid. Pure free acid is isolated from the organic phase, yield 1.0 g., m.p. 72°–74°.

EXAMPLE 30

3-[[(1-Methyl-1H-tetrazol-5-yl)thio]methyl]-8-oxo-7β-[[[[(phenylmethyl)thio]methyl]thio]acetyl]amino-5-thia-1-azabicyclo[4.2.0]oct-2-ene-2-carboxylic acid, sodium salt 0.6 g. of the product of Example 29 are dissolved in 10 ml. of methanol and 11 ml. of 0.1 N sodium bicarbonate solution are added. After stirring a while, it is filtered, the methanol is distilled off in vacuum and the residual aqueous solution is freeze dried to obtain 0.59 g. of 3-[[(1-Methyl-1H-tetrazol-5-yl)thio]methyl]-8-oxo-7β-[[[[(phenylmethyl)thio]methyl]thio]acetyl-]amino-5-thia-1-azabicyclo[4.2.0]oct-2-ene-2-carboxylic acid, sodium salt, m.p. 140°–145°.

EXAMPLES 31 – 56

The products below are obtained by reacting the acid

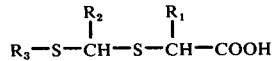

with the diphenylmethyl ester of one of the following according to the procedure of Example 26 and then following with the procedure of Example 27. Salts are produced by continuing with the procedure of Example 28.

3[[(5-methyl-1,3,4-thiadiazolyl-2-yl)thio]methyl]-7-amino-8-oxo-5-thia-1-azabicyclo[4.2.0]oct-2-ene-2-carboxylic acid
3-[[(1-methyl-1H-tetrazol-5-yl)thio]methyl]-7-ACA
3-[[(1,3,4-oxadiazol-2-yl)thio]methyl]-7-ACA
3-[[(5-ethyl-1,3,4-oxadiazol-2-yl)thio]methyl]-7-ACA
3-[[(1,2,3,4-tetrazol-5-yl)thio]methyl]-7-ACA
3-[[(1-ethyl-1H-tetrazol-5-yl)thio]methyl]-7-ACA
3-[[(3-methyl-1,2,4-thiadiazol-5-yl)thio]methyl]-7-ACA
3-[[(1,2,4-thiadiazol-3-yl)thio]methyl]-7-ACA
3-[[(5-butyl-1,2,4-thiadiazol-3-yl)thio]methyl]-7-ACA
3-[[(1,2,3,4-thiatriazol-5-yl)thio]methyl]-7-ACA
3-[[(5-methyl-1,3,4-oxadiazol-2-yl)thio]methyl]-7-ACA
3-[[(1,2,4-thiadiazol-5-yl)thio]methyl]-7-ACA
3-[[(4-pyridinyl-N-oxide)thio]methyl-7-ACA
3-[[(2-pyridinyl-N-oxide)thio]methyl]-7-ACA
3-[[(3-pyridinyl-N-oxide)thio]methyl]-7-ACA

| Example | |
|---|---|
| 31 | 7β-[[[[(n-butylthio)methyl]thio]-2-phenylacetyl]amino]-3-[[(1,3,4-oxadiazol-2-yl)thio]methyl]-8-oxo-5-thia-1-azabicyclo[4.2.0]oct-2-ene-2-carboxylic acid |
| 32 | 7β-[[[[(ethylthio)methyl]thio]-2-(2-furyl)acetyl]-amino]-3-[[(5-ethyl-1,3,4-oxadiazol-2-yl)thio]-methyl]-8-oxo-5-thia-1-azabicyclo[4.2.0]oct-2-ene-2-carboxylic acid |

-continued

| Example | |
|---|---|
| 33 | 7β-[[[[(ethylthio)methyl]thio]-2-(2-thienyl)acetyl-amino]-3-[[(1,2,3,4-thiatriazol-5-yl)thio]methyl]-8-oxo-5-thia-1-azabicyclo[4.2.0]oct-2-ene-2-carboxylic acid |
| 34 | 7β-[[[[2-(phenylmethylthio)methyl]thio]-2-phenyl-acetyl]amino]-3-(1,2,3,4,-tetrazol-5-yl)thio]methyl]-8-oxo-5-thia-1-azabicyclo[4.2.0]oct-2-ene-2-carboxylic acid |
| 35 | 7β-[[[[(propylthio)methyl]thio]-2-phenylacetyl]amino]-3-[[(1,2,4-thiadiazol-5-yl)thio]methyl]-8-oxo-5-thia-1-azabicyclo[4.2.0]oct-2-ene-2-carboxylic acid |
| 36 | 7β-[[[[(2-phenylethyl)thio]methyl]thio]acetyl]amino]-3-[[(1,2,4-thiadiazol-3-yl)thio]methyl]-8-oxo-5-thia-1-azabicyclo[4.2.0]oct-2-ene-2-carboxylic acid |
| 37 | 7β-[[[[(methylthio)methyl]thio]-2-phenylacetyl]-amino]-3-[[(5-butyl-1,2,4-thiadiazol-3-yl)thio-methyl]-8-oxo-5-thia-1-azabicyclo[4.2.0]oct-2-ene-2-carboxylic acid |
| 38 | 7β[[[(methylthio)methyl]thio]butyramido]-3-[[(1,2,3,4-tetrazol-5-yl)thio]methyl]-8-oxo-5-thia-1-azabicyclo[4.2.0]oct-2-ene-2-carboxylic acid |
| 39 | 7β-[[[(phenylmethylthio)methyl]thio]propionamido]-3-[[(1-methyl-1H-tetrazol-5-yl)thio]methyl]-8-oxo-5-thia-1-azabicyclo[4.2.0]oct-2-ene-2-carboxylic acid |
| 40 | 7β-[[[[(methylthio)methyl]thio]-2-phenylacetyl]-amino]-3-[[(5-methyl-1,3,4-oxadiazol-2-yl)thio]-methyl]-8-oxo-5-thia-1-azabicyclo[4.2.0]oct-2-ene-2-carboxylic acid |
| 41 | 7β-[[[[(methylthio)methyl]thio]acetyl]amino]-3-[[1-ethyl-1H-tetrazol-5-yl)thio]methyl]-8-oxo-5-thia-1-azabicyclo-[4.2.0]oct-2-ene-2-carboxylic acid |
| 42 | 7β-[[[[(methylthio)methyl]thio]-2-phenylacetyl]amino]-3-[[(1-ethyl-1H-tetrazol-5-yl)thio]methyl]-8-oxo-5-thia-1-azabicyclo[4.2.0]oct-2-ene-2-carboxylic acid |
| 43 | 7β-[[[[(ethylthio)methyl]thio]-2-phenylacetyl]-amino]-3-[[(5-methyl-1,3,4-thiadiazol-2-yl)thio]-methyl]-oxo-5-thia-1-azabicyclo[4.2.0]oct-2-ene-2-carboxylic acid |
| 44 | 7β-[[[[(ethylthio)methyl]thio]-2-(2-furyl)acetyl]-amino]-3-[[(5-methyl-1,3,4-thiadiazol-2-yl)thio]-methyl]-8-oxo-5-thia-1-azabicyclo[4.2.0]oct-2-ene-2-carboxylic acid and potassium salt |
| 45 | 7β-[[[[(propylthio)methyl]thio]-2-(2-thienyl)acetyl]-amino]-3-[[(1,3,4-oxadiazol-2-yl)thio]methyl]-8-oxo-5-thia-1-azabicyclo[4.2.0]oct-2-ene-2-carboxylic acid and sodium salt |
| 46 | 7β-[[[[(ethylthio)methyl]thio]acetyl]amino]-3-[[(5-ethyl-1,3,4-oxadiazol-2-yl)thio]methyl]-8-oxo-5-thia-1-azabicyclo[4.2.0]oct-2-ene-2-carboxylic acid |
| 47 | 7β-[[[[(n-butylthio)methyl]thio]acetyl]amino]-3-[[(1,2,3,4-tetrazol-5-yl)thio]methyl]-8-oxo-5-thia-1-azabicyclo[4.2.0]oct-2-ene-2-carboxylic acid |
| 48 | 7β-[[[[(phenylmethylthio)methyl]thio]-2-(3-furyl)-acetyl]amino]-3-[[(1,2,4-thiadiazol-3-yl)thio]methyl]-8-oxo-5-thia-1-azabicyclo[4.2.0]oct-2-ene-2-carboxylic acid pivaloyloxymethyl ester |
| 49 | 7β-[[[[(methylthio)methyl]thio]-2-(2-furyl)]acetyl]-amino]-3-[[(1,2,3,4-thiatriazol-5-yl)thio]methyl]-8-oxo-5-thia-1-azabicyclo[4.2.0]oct-2-ene-2-carboxylic acid trimethylsilyl ester |
| 50 | 7β-[[[[(methylthio)methyl]thio]-2-(2-thienyl)acetyl]-amino]-3-[[(1,3,4-oxadiazol-2-yl)thio]methyl]-8-oxo-5-thia-1-azabicyclo[4.2.0]oct-2-ene-2-carboxylic acid phenylmethyl ester |
| 51 | 7β-[[[[(ethylthio)methyl]thio]-2-phenylacetyl]amino]-3-[[(2-pyridinyl-N-oxide)thio]methyl]-8-oxo-5-thia-1-azabicyclo[4.2.0]oct-2-ene-2-carboxylic acid |
| 52 | 7β-[[[[(phenylmethylthio)methyl]thio]-2-phenylacetyl]amino]-3-[[(2-pyridinyl-N-oxide)thio]methyl]-8-oxo-5-thia-1-azabicyclo[4.2.0]oct-2-ene-2-carboxylic acid pivaloyloxymethyl ester |
| 53 | 7β-[[[[(methylthio)methyl]thio]acetyl]amino]-3-[[(4-pyridinyl-N-oxide)thio]methyl]-8-oxo-5-thia-1-azabicyclo[4.2.0]oct-2-ene-2-carboxylic acid and potassium salt |
| 54 | 7β-[[[[(methylthio)methyl]thio]-2-phenylacetyl]amino]-3-[[(5-methyl-1,3,4-thiadiazol-2-yl)thio]methyl]-8-oxo-5-thia-1-azabicyclo[4.2.0]oct-2-ene-2-carboxylic acid and sodium salt |
| 55 | 7β-[[[1-(methylthio)ethyl]thio]acetyl]amino-3-[[(1-methyl-1H-tetrazol-5-yl)thio]methyl]-8-oxo-5-thia-1-azabicyclo[4.2.0]oct-2-ene-2-carboxylic acid |
| 56 | 7β-[[[1-(phenylthio)propyl]thio]phenylacetyl]amino-3-[[(1-methyl-1H-tetrazol-5-yl)thio]methyl]-8-oxo-5-thia-1-azabicyclo[4.2.0]oct-2-ene-2-carboxylic acid. |

What is claimed is:

1. A compound of the formula

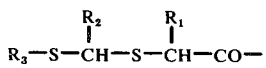

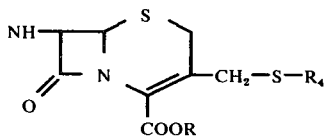

wherein R is hydrogen, lower alkyl, phenyl-lower alkyl, benzhydryl, tri(lower alkyl)silyl, alkali metal, alkaline earth metal, triethylamine salt, (lower alkyl)amine salt or

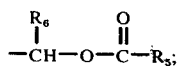

$R_1$ is hydrogen, lower alkyl, phenyl, thienyl or furyl; $R_2$ and $R_6$ each is hydrogen or lower alkyl; $R_3$ and $R_5$ each is lower alkyl, phenyl or phenyl-lower alkyl; $R_4$ is oxadiazolyl, thiadiazolyl, thiatriazolyl, tetrazolyl, 1oxopyridinyl or their lower alkyl derivatives; said lower alkyl groups having up to eight carbon atoms.

2. A compound as in claim 1 wherein $R_1$ is phenyl.

3. A compound as in claim 1 wherein $R_1$ is hydrogen.

4. A compoud as in claim 1 wherein R and $R_2$ each is hydrogen, $R_1$ is phenyl and $R_3$ is lower alkyl.

5. A compound as in claim 1 wherein R is hydrogen or alkali metal; $R_1$ is phenyl; $R_2$ is hydrogen; $R_3$ is lower alkyl; and $R_4$ is (lower alkyl)tetrazolyl.

6. A compound as in claim 5 wherein each lower alkyl group is methyl and R is hydrogen.

7. A compound as in claim 5 wherein each lower alkyl group is methyl and R is alkali metal.

8. A compound as in claim 7 wherein the alkali metal is sodium.

9. A compound as in claim 1 wherein R is hydrogen or alkali metal, $R_1$ is hydrogen or phenyl, $R_2$ is hydrogen, $R_3$ is lower alkyl and $R_4$ is (lower alkyl)thiadiazolyl.

10. A compound as in claim 1 wherein R, $R_1$ and $R_2$ each is hydrogen, $R_3$ is lower alkyl and $R_4$ is (lower alkyl)tetrazolyl.

11. A compound as in claim 10 wherein each lower alkyl group is methyl.

12. A compound as in claim 1 wherein R, $R_1$ and $R_2$ each is hydrogen, $R_3$ is phenyl and $R_4$ is (lower alkyl)tetrazolyl.

13. A compound as in claim 12 wherein the lower alkyl group is methyl.

* * * * *